(12) United States Patent
Sagel et al.

(10) Patent No.: US 9,198,841 B2
(45) Date of Patent: Dec. 1, 2015

(54) STRUCTURES AND COMPOSITIONS INCREASING THE STABILITY OF PEROXIDE ACTIVES

(75) Inventors: Paul Albert Sagel, Maineville, OH (US); Hooman Shahidi, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1131 days.

(21) Appl. No.: 12/393,647

(22) Filed: Feb. 26, 2009

(65) Prior Publication Data

US 2009/0214448 A1   Aug. 27, 2009

Related U.S. Application Data

(63) Continuation of application No. 11/181,329, filed on Jul. 14, 2005, now abandoned, which is a continuation of application No. 10/279,656, filed on Oct. 24, 2002, now Pat. No. 7,018,622, which is a continuation of application No. 09/675,767, filed on Sep. 29, 2000, now abandoned, which is a continuation-in-part of application No. 09/605,774, filed on Jun. 28, 2000, now Pat. No. 6,582,708, and a continuation-in-part of application No. 09/605,220, filed on Jun. 28, 2000, now abandoned, which is a continuation of application No. 09/196,364, filed on Nov. 19, 1998, now Pat. No. 6,096,328, which is a continuation-in-part of application No. 08/870,664, filed on Jun. 6, 1997, now Pat. No. 5,894,017, said application No. 09/605,220 is a continuation-in-part of application No. 09/268,171, filed on Mar. 15, 1999, now Pat. No. 6,277,458.

(51) Int. Cl.
| | | |
|---|---|---|
| *A61K 9/00* | (2006.01) | |
| *A61K 8/22* | (2006.01) | |
| *A61C 19/06* | (2006.01) | |
| *A61K 8/02* | (2006.01) | |
| *A61Q 11/00* | (2006.01) | |

(52) U.S. Cl.
CPC ............... *A61K 8/22* (2013.01); *A61C 19/063* (2013.01); *A61C 19/066* (2013.01); *A61K 8/0208* (2013.01); *A61K 9/006* (2013.01); *A61K 9/0063* (2013.01); *A61Q 11/00* (2013.01)

(58) Field of Classification Search
CPC .................................................... A61K 9/0056
USPC .................................................. 433/42; 429/401
See application file for complete search history.

(56) References Cited

U.S. PATENT DOCUMENTS

| | | | | |
|---|---|---|---|---|
| 5,211,559 | A * | 5/1993 | Hart et al. | 433/80 |
| 5,234,342 | A * | 8/1993 | Fischer | 433/215 |
| 5,863,202 | A * | 1/1999 | Fontenot et al. | 433/215 |
| 5,879,691 | A * | 3/1999 | Sagel et al. | 424/401 |

* cited by examiner

*Primary Examiner* — Benjamin Packard
(74) *Attorney, Agent, or Firm* — Amanda T. Barry

(57) ABSTRACT

A tooth whitening system is provided. The tooth whitening system includes a carrier, first and second substrates, and first and second tooth whitening compositions.

20 Claims, 5 Drawing Sheets

STRUCTURES AND COMPOSITIONS INCREASING THE STABILITY OF PEROXIDE ACTIVES

This application is a continuation of U.S. application Ser. No. 11/181,329, filed on Jul. 14, 2005, which is a continuation of U.S. application Ser. No. 10/279,656 filed Oct. 24, 2002, now U.S. Pat. No. 7,018,622; which is a continuation of U.S. application Ser. No. 09/675,767 filed Sep. 29, 2000, now abandoned; which is a continuation-in-part of U.S. application Ser. No. 09/605,774 filed Jun. 28, 2000, now U.S. Pat. No. 6,582,708; and a continuation-in-part of U.S. application Ser. No. 09/605,220 filed Jun. 28, 2000, now abandoned; which is a continuation of U.S. application Ser. No. 09/196,364 filed Nov. 19, 1998, now U.S. Pat. No. 6,096,328; which is a continuation-in-part of U.S. application Ser. No. 08/870,664 filed Jun. 6, 1997, now U.S. Pat. No. 5,894,017; and a continuation-in-part of U.S. application Ser. No. 09/268,171 filed Mar. 15, 1999, now U.S. Pat. No. 6,277,458, the substances of which are fully incorporated herein by reference.

TECHNICAL FIELD OF THE INVENTION

The present invention relates to structures and compositions increasing the stability of whitening actives, and, more particularly, to structures and compositions for use with tooth whitening systems comprising a tooth whitening composition.

BACKGROUND OF THE INVENTION

Tooth whitening has become very popular over the past few years. More and more consumers are choosing to whiten their teeth. Options for tooth whitening include toothpastes, mouthrinses, chewing gums, in-office bleaching, and most commonly tooth whitening solutions used with a tray obtained either over-the-counter or from a dentist. The tooth whitening solutions contain an active ingredient which bleach the teeth. This solution is placed into a dental tray in which a patient wears to bleach his or her teeth. Typically, the oral composition comes in a squeeze bottle, tube, or syringe.

It is known that tooth whitening active materials may be difficult to keep stable for long periods of time. The most common dental bleaching agents are peroxides, which are known to be very reactive. To improve stability, a peroxide may be encapsulated, formulated in a two part composition, or stabilizers added to maintain peroxide levels. Generally, the peroxide compositions are stored in sealed, bulk containers, such as a syringe or tube.

Non-bulk, tooth whitening systems comprising a strip and a pre-dosed amount of a tooth whitening composition are described in U.S. Pat. Nos. 5,984,017; 5,879,691; 5,891,453; 6,045,811; and 5,989,569, the substances of which are fully incorporated herein by reference. These improved systems provide a disposable and more user friendly means for tooth whitening. However, the peroxide containing oral composition is more difficult to stabilize for extended periods of time because the oral composition is stored as a thin layer and not in a syringe or in bulk.

SUMMARY OF THE INVENTION

In one embodiment, the present invention is directed to a tooth whitening system which includes a carrier, a first substrate and a first tooth whitening composition, a second substrate and a second tooth whitening composition, and a package. The first and second tooth whitening are disposed on the carrier.

In another embodiment, the present invention is directed to a tooth whitening system. The tooth whitening system includes a carrier, a first substrate and a first tooth whitening composition, and a second substrate and a second tooth whitening composition, wherein the tooth whitening compositions are disposed on the carrier.

In a third embodiment, the present invention is directed to a tooth whitening system including a carrier, a first substrate in the form of a strip and a first tooth whitening composition, and a second substrate in the form of a strip and a second tooth whitening composition. The first and second tooth whitening compositions are disposed on the carrier and the carrier is capable of being separated from the tooth whitening compositions prior to application.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE PREFERRED EMBODIMENTS

Reference will now be made in detail to the present preferred embodiments of the invention, examples of which are illustrated in the accompanying drawings wherein like numerals indicate the same elements throughout the views and wherein elements having the same two last digits (e.g., 20 and 120) or alphabetic suffix (e.g., 22A and 22B) connote similar elements. As discussed more fully hereafter, the present invention is directed to means which increase the stability of a peroxide active. As used herein, the term "stability" is intended to refer to the propensity of a peroxide active (or other non-stable active) to maintain its original concentration over a fixed period of time (e.g., three months, six months, twelve months, etc.), wherein the fixed period of time is measured beginning from the point at which tooth whitening composition is manufactured and formed as a thin layer. Even small to moderate increases in the stability of a peroxide active can have a significant impact on the shelf life of a peroxide system. For example, moving from a peroxide system having a composition which retains 28% of its original 6% concentration of a peroxide active after twelve months to a peroxide system having 39% of its original 6% concentration of the peroxide active after twelve months would allow the latter peroxide system to remain on a store shelf for an additional three months before reaching a minimum effective concentration of 3%.

Figure 1:
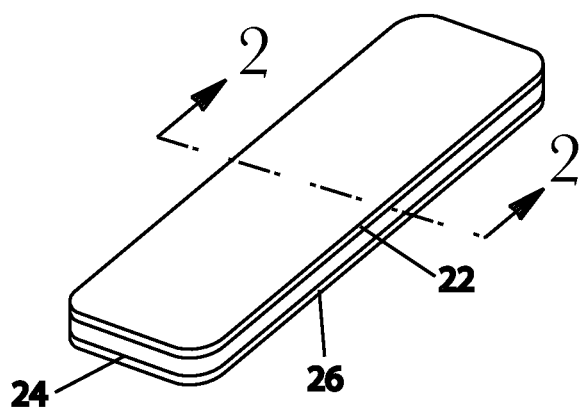
FIG. 1 is a perspective view of a preferred tooth whitening system made in accordance with the present invention.

A particularly preferred embodiment of the present invention is illustrated in FIG. 1 and is directed to a tooth whitening system 20 comprising a substrate 22, a thin layer 24 of a tooth whitening composition comprising a peroxide active, and a carrier 26. The substrate 22 is used to apply the tooth whitening composition to the teeth and serves as a protective barrier to substantially prevent saliva from contacting the tooth whitening composition as well as preventing erosion of the tooth whitening composition from the surface of the teeth by the wearer's lips, tongue, and other soft tissue. The carrier 26 also serves as a protective barrier, but the substrate 22 and the thin layer 24 are separated from the carrier 26 prior to application of the tooth whitening composition to the teeth, thereby exposing the thin layer 24 for use. The means for increasing the stability of the tooth whitening composition can be the concentration of a polyol, the ratio of the exposed surface area of the thin layer 24 to the volume of the thin layer 24, the ratio of the unexposed surface area 24 of the thin layer to the volume of the thin layer 24, the material forming at least a portion of the surface of the substrate 22 or the carrier 26 which is in contact with the composition, the ratio of the volume of head space of a package to the volume of the thin layer 24, and combinations thereof as well as all equivalents thereof. While the present invention will be discussed herein with respect to the tooth whitening system 20 for simplicity, it will be appreciated that the present invention can be applied to other oral compositions containing a peroxide active, such as tartar control compositions, remineralization compositions, antiseptic compositions, gingivitis compositions, healing compositions, and the like. It is also contemplated that the present invention is suitable for use with other systems comprising a peroxide active, such as fabric bleaching systems, hair bleaching systems, topical disinfecting systems, etc. Still further, it is contemplated that the present invention could be used with compositions comprising other non-stable or volatile actives, such as alcohol, ethanol, ethers, menthol and other flavors, methyl salicylate, etc.

The tooth whitening composition contains a peroxide active and is provided in as the thin layer 24 between the carrier 26 and the substrate 22. The term "thin layer", as used herein, is intended to refer to the physical formation or position of the tooth whitening composition. The thin layer 24 of tooth whitening composition is generally on or in contact with the substrate 22 and carrier 26. The thin layer 24 of tooth whitening composition may be stored, coated, or spread on the carrier 26. The thin layer 24 of tooth whitening composition preferably has a thickness between about 0.01 mm and about 3 mm, more preferably between about 0.02 mm and about 2 mm, most preferably between about 0.05 mm and about 1 mm, and still more most preferably between about 0.07 mm and about 0.5 mm. These measurements are taken by measuring from the surface 28 of the carrier 26 and up through the thin layer 24 of tooth whitening composition. While it is desirable for the thin layer of the tooth whitening composition to be a homogeneous, uniform and continuous layer, the thin layer 24 may also be non-uniform, non-continuous, and/or heterogeneous. For example, the thin layer 24 can be a laminate or separated layers of components, an amorphous mixture of components, separate stripes or spots or other patterns of different components, or a combination of these structures.

The tooth whitening composition of the present invention can be provided in the form of a viscous liquid, paste, gel, solution, or any other state or phase that can form a thin layer. Preferably, the tooth whitening composition is provided in the form of a gel and has a viscosity between about 200 and about 1,000,000 cps at low shear rates (approximately one seconds$^{-1}$). More preferably, the viscosity is between about 100,000 and about 800,000 cps and most preferably is between about 150,000 and about 700,000 cps. Still more most preferably, the viscosity is between about 300,000 and about 700,000 cps.

The amount of tooth whitening composition provided with the tooth whitening system 20 will vary depending upon the intended use, the size of the substrate 22, concentration of the peroxide active, and the desired benefit. Generally, less than about 1 gram of tooth whitening composition is required in tooth whitening applications. Preferably, from about 0.05 grams to about 0.5 grams and more preferably from about 0.1 gram to about 0.4 grams of the tooth whitening composition is provided. The amount of tooth whitening composition per square cm of substrate 22 is less than about 0.2 grams/cm$^2$, preferably from about 0.005 to about 0.1 grams/cm$^2$, and more preferably from about 0.01 grams/cm$^2$ to about 0.05 grams/cm$^2$.

As known in the art, the tooth whitening composition also has a yield stress. Yield stress is the amount of force on a material before the material begins to move. The yield stress must be high enough so that the tooth whitening composition is able to form a thin layer and also to handle the disturbances caused by manufacturing, handling, and storage. The yield stress of the tooth whitening composition is between about 2 Pascals and about 3000 Pascals, preferably between about 20 Pascals and about 2000 Pascals, more preferably between about 200 Pascals and about 1500 Pascals, and most preferably between about 400 Pascals and about 1200 Pascals.

The peroxide actives suitable for use with the present invention include hydrogen peroxide, calcium peroxide, carbamide peroxide, and mixtures thereof. Most preferred is hydrogen peroxide. Other peroxide actives include compositions which produce hydrogen peroxide when mixed with water, such as the percarbonates, specifically sodium percarbonate. While the peroxide active can be present in any concentration, it is preferred that the peroxide active is present in an concentration between about 0.01% and about 40%, by weight of the tooth whitening composition in tooth whitening applications. The peroxide active should provide an concentration of hydrogen peroxide equivalent between about 0.1% and about 20%, preferably between about 0.5% and about 15%, more preferably between about 1% and about 10%, and most preferably between about 2% and about 10% by weight of the tooth whitening composition. It is understood that these concentrations are expressed for hydrogen peroxide and appropriate conversions must be made for other peroxide liberating molecules such as carbamide peroxide, calcium peroxide, etc.

Additional constituents of the tooth whitening composition can include, but are not limited to, water, gelling agents, humectants, pH adjusting agents, stabilizing agents, desensitizing agents, and accelerating agents or bleach activators. In addition to the above materials, a number of other materials can also be added to the substance. Additional materials include, but are not limited to, flavoring agents, sweetening agents such as saccharin, xylitol, opacifiers, coloring agents, and chelants such as ethylenediaminetetraacetic acid. These additional ingredients can also be used in place of the compounds disclosed above.

Gelling agents suitable for use do not react with or inactivate the constituents of the oral care composition. A common gelling agent is a swellable polymer. An effective concentration of a gelling agent to enable the tooth whitening composition to form a thin layer will vary with each type of gelling agent. The thin layer will have a viscosity and yield stress enabling the tooth whitening composition to form the thin layer on a carrier. The tooth whitening composition formed with these agents may also provide sufficient adhesive attachment of the film material to the targeted area of the mouth. For example, the level of gelling agent to form the tooth whitening composition with a carboxypolymethylene is between about 0.1% and about 15%, preferably between about 1% and about 10%, more preferably between about 2% and about 8%, and most preferably between about 3% and about 6%, by weight of the tooth whitening composition. An effective concentration of a poloxamer gelling agent is between about 10% and about 40%, preferably between about 20% and about 35%, and more preferably between about 25% and about 30%, by weight of the tooth whitening composition.

Suitable gelling agents useful in the present invention include "Pemulen" made by B. F. Goodrich Company, carboxypolymethylene, carboxymethyl cellulose, carboxypropyl cellulose, hydroxyethyl cellulose, poloxamer, Laponite, carrageenan, Veegum, carboxyvinyl polymers, and natural gums such as gum karaya, xanthan gum, Guar gum, gum arabic, gum tragacanth, and mixtures thereof. The preferable gelling agent for use in the present invention is carboxypolymethylene, obtained from B. F. Goodrich Company under the tradename "Carbopol". Particularly preferable Carbopols include Carbopol 934, 940, 941, 956, 971, 974, 980, and mixtures thereof. Particularly preferred is Carbopol 956. Carboxypolymethylene is a slightly acidic vinyl polymer with active carboxyl groups.

Other suitable gelling agents include both polymers with limited water solubility as well as polymers lacking water solubility. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

A pH adjusting agent may also be added to make the composition safe for oral tissues. These pH adjusting agents, or buffers, can be any material which is suitable to adjust the pH of the composition. Suitable materials include sodium bicarbonate, sodium phosphate, sodium hydroxide, ammonium hydroxide, potassium hydroxide, sodium stannate, triethanolamine, citric acid, hydrochloric acid, sodium citrate, and combinations thereof. The pH adjusting agents are added in sufficient concentrations so as to adjust the pH of the composition to between about 3 and about 10, preferably between about 4 and about 8.5, and more preferably between about 4.5 and about 8. The pH adjusting agents are generally present in an concentration between about 0.01% and about 15% and preferably between about 0.05% and about 5%, by weight of the composition.

Suitable stabilizing agents include benzoic acid, salicylic acid, butylated hydroxytoluene, tin salts, phosphates, and others. Suitable bleach activators include trichloroisocyanuric acid and the phosphates, such as tetrasodium pyrophosphate.

Desensitizing agents may also be used in the tooth whitening composition. These agents may be preferred for consumers who have sensitive teeth. Desensitizing agents include potassium nitrate, citric acid, citric acid salts, strontium chloride, and combinations thereof. Potassium nitrate is a preferred desensitizing agent. Other agents which provide the benefit of reduced tooth sensitivity are also included in the present invention. Typically, the concentration of a desensitizing agent is between about 0.01% and about 10%, preferably between about 0.1% and about 8%, and more preferably between about 1% and about 7% by weight of the tooth whitening composition.

The substrate 22 may be formed from materials such as polymers, natural and synthetic wovens, non-wovens, foil, paper, rubber, and combinations thereof. The substrate 22 (as well as the carrier 26) may be a single layer of material or a laminate of more than one layer. Suitable polymers include, but are not limited to, ethylvinylacetate, ethylvinyl alcohol, polyesters such as MYLAR® manufactured by DuPont, and combinations thereof.

The carrier can be formed from any material which exhibits less affinity for the tooth whitening composition than the tooth whitening composition exhibits for itself and for the substrate 22. For example, the carrier 26 can be formed from paper or a polyester, such as SCOTCHPAK® which is manufactured by the 3M Corp. of Minneapolis, Minn., which are coated with a non-stick material in order to aid release of the tooth whitening composition from the carrier 26 when the substrate 22 is pulled away from the carrier 26. Exemplary coatings can include wax, silicone, fluoropolymers such as Teflon®, fluorosilicones, or other non-stick type materials. Also, suitable coatings might include one of the coatings described in U.S. Pat. Nos. 3,810,874; 4,472,480; 4,567,073; 4,614,667; 4,830,910; and 5,306,758, the substances of which are incorporated herein by reference. A further description of materials suitable which might be suitable as release agents is found in Kirk-Othmer Encyclopedia of Chemical Technology, Fourth Edition, Volume 21, pp. 207-218, incorporated herein by reference.

While the tooth whitening system 20 is described herein as comprising both the substrate 22 and the carrier 26, it is contemplated that the tooth whitening system 20 (or other peroxide systems within the scope of the present invention) may comprise only the substrate 22 and the thin layer 24. For example, the interior of a package storing the substrate 22 and the thin layer 24 might be coated in a manner similar to that described above with respect to the carrier 26 to facilitate removal of the substrate 22 and the thin layer from the package during use. Further, it is contemplated that the tooth whitening system 20 could be provided in the form of a roll rather than planar as shown herein and could comprise a plurality of substrates and/or carriers. Alternatively, it is contemplated that the substrate 22 and/or carrier 26 might include other non-planar shapes such as preformed dental trays or flexible dental trays. The substrate and/or carrier can also be formed from permanently deformable strips of material, wax, or any other material suitable for use as a barrier for the tooth whitening composition and for applying the tooth whitening composition to the teeth.

While the above-described materials for the substrate 22 and carrier 26 are suitable for use with the present invention, the stability of the peroxide active of the thin layer 24 of the tooth whitening composition is improved when the carrier 26 and/or the substrate 22 (or at least the surfaces 28 and/or 30 in contact with the peroxide active) are formed from a polyolefin and, preferably, from polyethylene or polypropylene. While these materials are preferred, it is believed that polyolefin blends, polyethylene blends, polypropylene blends, and combinations thereof would also be suitable for use as the substrate 22 and/or the carrier 26 in the present invention. As discussed above, the carrier 26 can also be coated to aid release of the tooth whitening composition from the carrier 26 during manufacture and/or use. However, these coatings generally do not act as barriers between the peroxide active and underlying material such that proper selection of the underlying material is still desirable. Any coating should be inert, however, relative to the peroxide active.

It has further been found that the stability of a peroxide is negatively affected by the presence of polyester, especially in the presence of a polyol. Therefore, at least the portion of the surfaces 28 and 30 of the substrate 22 and/or the carrier 26 which are in contact with the tooth whitening composition are preferably formed from materials other than polyester so that a material comprising polyester does not contact the tooth whitening composition. More preferably, the substrate 22 and/or the carrier 26 are formed completely from materials other than polyester. While it has been found that polyester and a peroxide active have a negative interaction in the absence of a polyol, the combination of all three components results in a further negative synergy with respect to the stability of the peroxide active.

The substrate 22 and/or carrier 26 are generally less than about 1 mm thick, preferably less than about 0.05 mm thick, and more preferably from about 0.001 to about 0.03 mm thick. Still more preferably, the substrate 22 and/or carrier 26 are less than about 0.1 mm thick and yet more preferably from about 0.005 to about 0.02 mm thick. The thickness and the permeability of the substrate 22 and/or carrier 26 may have an effect on the stability of the tooth whitening composition. In general, a thicker strip may provide more stability for the tooth whitening composition. However, the thickness of the substrate must be balanced with the consumer acceptance of comfort of wearing the strip.

While the substrate 22 can be sized according to its application, in the tooth whitening system 20, the substrate is sized to individually fit the tooth or row of teeth desired to be bleached. Generally, this is the front, six to eight teeth of the upper or lower rows of teeth that are visible when the wearer is smiling or either the maxillary dentition or the mandibular dentition. Optionally, the substrate 22 may fit the entire upper or lower rows of teeth when positioned against the teeth. Most preferably, the substrate 22 is sized to overlap with one of the gingival margins and is further sized to cover at least the central six anterior teeth (cuspid to cuspid). The substrate 22 can be a maxillary strip which is rectangular with rounded corners and measures approximately 6.5 cm long×1.5 cm wide and/or the substrate 22 can be a mandibular strip which is trapezoidal with rounded corners and measures 5.0 cm long×2.0 cm wide. Further description of the size and shape of the substrate 22 in a tooth whitening application is disclosed in U.S. patent application Ser. No. 09/268,185 filed Mar. 15, 1999, the substance of which is fully incorporated herein by reference. While the carrier 26 should be at least the same size and shape as the substrate 22 as shown in FIG. 1, the carrier 26 can extend beyond the substrate as shown by way of example in FIG. 4 so that it is easier to the carrier 26 and remove the substrate 22 and the thin layer 24 from the carrier 26.

The substrate 22 should have a relatively low flexural stiffness so as to enable it to drape over the contoured surfaces of the teeth with very little force being exerted; that is, conformity to the curvature of the wearer's mouth, teeth, and gaps between teeth is maintained because there is little residual force within the substrate to cause it to return to its substantially flat shape. The flexibility of the substrate enables it to contact adjoining soft tissue over an extended period of time without physical irritation. The substrate does not require pressure to form it against the teeth and it is readily conformable to the tooth surfaces and the interstitial tooth spaces without permanent deformation when it is applied.

Flexural stiffness is a material property that is a function of a combination of strip thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In a preferred embodiment but not required for the present invention, the flexible substrate has a flexural stiffness of less than about 5 grams/cm as measured on a Handle-O-Meter, model #211-300, available from Thwing-Albert Instrument Co. of Philadelphia, Pa., as per test method ASTM D2923-95. Preferably, the substrate 22 has a flexural stiffness less than about 4 grams/cm, more preferably less than about 3 grams/cm, and most preferably from about 0.1 grams/cm to about 1 grams/cm.

For a tooth whitening composition, it is often desirable to include a humectant as a constituent of the composition. A humectant provides rheological and/or physical stability and provides various aesthetics for a user. However, for common humectants such as polyols (e.g., glycerin, sorbitol, polyethylene glycol, propylene glycol), the stability of the peroxide active is negatively affected by large concentrations of the humectant, especially in the presence of polyester. Therefore, in accordance with yet another aspect of the present invention, a polyol of the thin layer 24 of the tooth whitening composition is present in an concentration less than about 40%, preferably between about 0% and about 35%, more preferably between about 1% and about 30%, and most preferably between about 5% and about 15%, by weight of the tooth whitening composition. Further, these low polyol concentrations are further preferably used in combination with a carrier 26 and/or substrate 22 having surfaces 28 and 30 in contact with the tooth whitening composition which are formed from materials other than polyester. More preferably, these low polyol concentrations are present in combination with a carrier 26 and/or substrate 22 having surfaces 28 and 30 in contact with the tooth whitening composition which are formed from a polyolefin.

Figure 3:
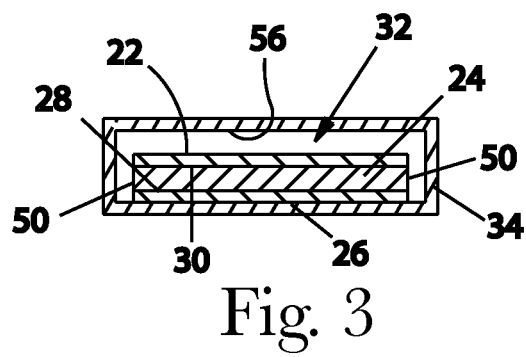
FIG. 3 is a cross-sectional side elevational view of the preferred tooth whitening system of FIG. 1 disposed within a package.

As the concentration of polyol decreases, balance of the tooth whitening composition can comprise water in a concentration between about 65% and about 99%, preferably between about 70% and about 95%, and more preferably between about 70% and about 90% by weight of the total tooth whitening composition. This concentration of water includes the free water that is added plus that amount that is introduced with other materials. The increased water composition improves peroxide stability as it relates to the liquid phase of the composition and physical chemistry (e.g., the vapor/liquid equilibrium state) of the composition. Chemically, as the water concentration goes up, it is replacing glycerin. As the water concentration increases, the mole ratio of peroxide relative to water decreases. This lowers the vapor equilibrium concentration of peroxide in the vapor phase. In a fixed head space system (e.g., in package 34 of FIG. 3), less total peroxide will be in the vapor phase. Peroxide reacts in the vapor phase. Thus, lowering the polyol concentration lowers the reaction rate in the vapor phase. This also slows decomposition of the peroxide in the gel phase as it is the reservoir for maintaining the headspace equilibrium. Therefore, increasing the water level of the formulation slows the liquid phase chemical reaction decomposition and slows the vapor phase decomposition, thereby maintaining a higher concentration of peroxide over a given period of time.

In accordance with still yet another aspect of the present invention, it has been found that the stability of the thin layer 24 of the tooth whitening composition can be improved by appropriate selection of the exposed surface area and volume of the thin layer 24. As used herein, the term "exposed surface area" is intended to refer to the side surface area of the thin layer 24 of the tooth whitening composition (shown by way of example in the figures as reference numeral 50) which is directly exposed to head space 32 of a closed package 34 (FIG. 34) while the volume refers to the volume of the thin layer 24 of the tooth whitening composition. As used herein, the phrase "head space" is intended to refer to the empty volume (i.e., without the tooth whitening system) of the package 34. For example, a thin layer 24 having a length of 5 mm, a width of 5 mm, and a thickness of 0.1 mm and which has only the side surface area 50 exposed to the head space 32 would have an exposed surface area of 0.2 $mm^2$ and a volume of 0.25 $mm^3$. The ratio of the exposed surface area of the thin layer 24 to the volume of the thin layer 24 is less than about 0.15 $mm^{-1}$ and, more preferably, is between about 0.05 $mm^{-1}$ and about 0.15 $mm^{-1}$. Most preferably, the ratio of the exposed surface are of the thin layer 24 to the volume of the thin layer 24 is between about 0.05 $mm^{-1}$ and about 0.1 $mm^{-1}$.

The package 34 can be provided in a variety of shapes and sizes. However, it is desirable that the shape and size of the package 34 closely conform to the shape and size of the tooth whitening system 20. The package can be provided in the form of a pouch, a box, a plastic container, an envelope, a bag, or other suitable package known in the art. A plurality of packages 34 and tooth whitening systems 20 can be bundled or otherwise provided as a set so that a sufficient supply of tooth whitening systems is available for multi-day use. More preferably, the volume of the headspace 32 of the package 34 is between about 0.1 $mm^3$ and about 30,000 $mm^3$ and, more preferably, is between about 50 $mm^3$ and about 10,000 $mm^3$. The ratio of the volume of the head space 32 to the volume of the thin layer 24 is between 1 and about 500 and, preferably, is between 1 and about 400. More preferably, the ratio of the volume of the head space 32 to the volume of the thin layer 24 is between 1 and about 200 and most preferably is between 1 and about 100. The package 34 should be made of a material that is not translucent, has low or no moisture permeability, and is generally impermeable. The package 34 may be made of one or more materials and may optionally have a liner. For example, a pouch could be made of foil and have a polyethylene lining. Other suitable materials that are not translucent and prevent moisture permeability include plastic, paper, foil, cardboard, polymers, and rubbers. A secondary package (not shown) can also be provided which stores a plurality of the packages 34.

Figure 4:
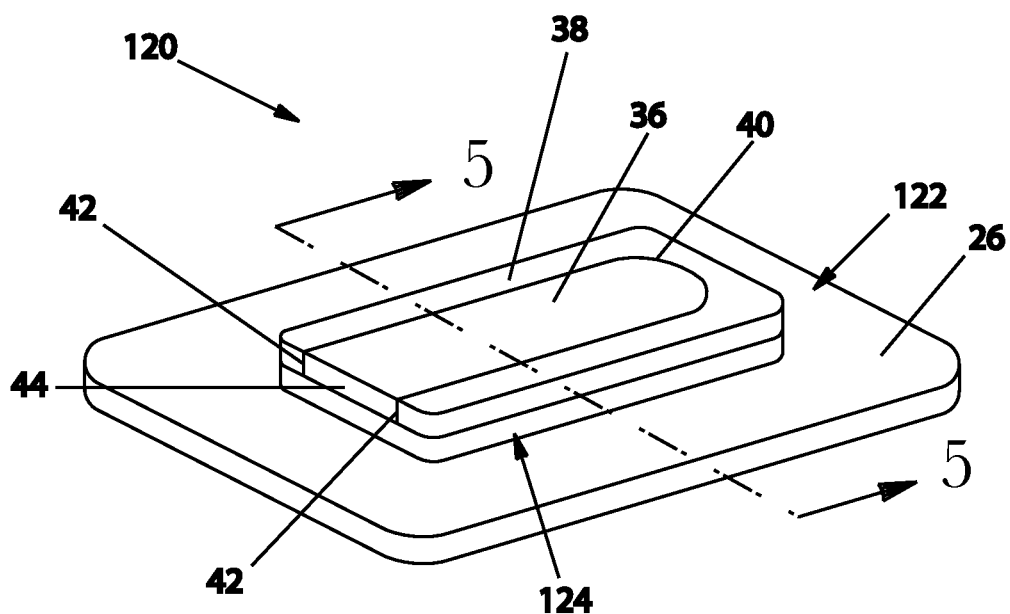
FIG. 4 is a perspective view of another preferred tooth whitening system made in accordance with the present invention.
Figure 5:
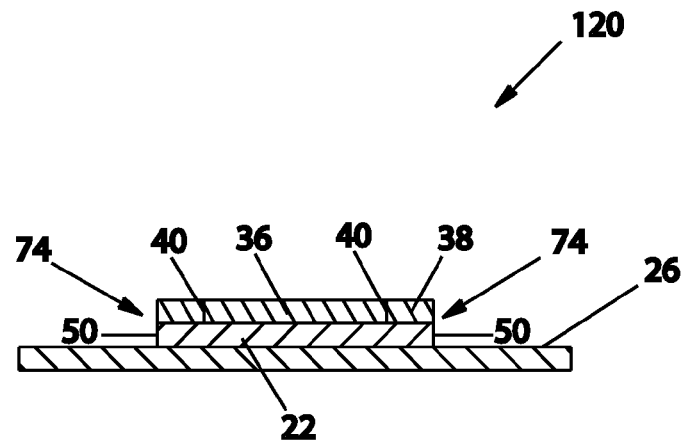
FIG. 5 is a cross-sectional side elevational view of the tooth whitening system of FIG. 4, taken along line 5-5 thereof.
Figure 6:
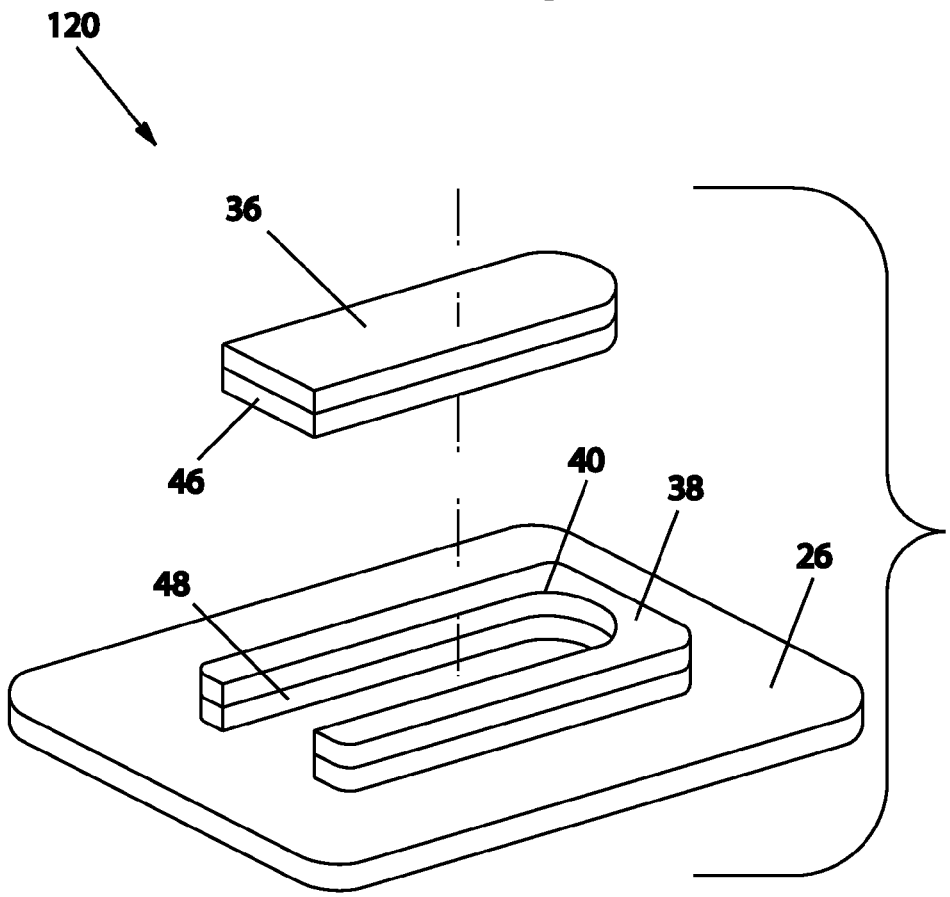
FIG. 6 is a perspective view of the tooth whitening system of FIG. 4, wherein a first portion of the substrate has been removed.

Referring to FIGS. 4 to 6, a preferred embodiment of the present invention which minimizes the ratio of the exposed surface area of the thin layer 24 to the volume of the thin layer 24 will now be described. The tooth whitening system 120 comprises a substrate 122 having a first section 36 which is applied to the teeth and a second section 38 remains with the carrier 26. The first and second sections 36 and 38 are separated by a slit 40 which preferably passes through the thickness of the substrate 122, although a frangible or otherwise partible separation (e.g., a perforated line, a partial slit, etc.) can be employed in place of the slit 40 such that the first and second sections 36 and 38 of the substrate 122 remain at least partially interconnected until fully separated by a user. The slit 40 is preferably substantially unshaped in top plan view, wherein both ends 42 of the slit 40 extend from a common edge 44 of the substrate 122. While this arrangement is preferred, it will be appreciated that other slit arrangements can be provided. The first and second sections 36 and 38 of the substrate 122 overlie first and second sections 46 and 48, respectively, of the thin layer 124 of the tooth whitening composition, as best seen in FIG. 6. In other words, the first section 46 of the tooth whitening composition is substantially coextensive with the first section 36 of the substrate 122 while the second section 48 of the tooth whitening composition is substantially coextensive with the second section 38 of the substrate 122. The first and second sections 46 and 48 of the tooth whitening composition are preferably integral with each other until separation during use in order to enhance the stabilizing effect of the second section 42. However, it is appreciated that partial or full separation between the first and second sections 46 and 48 of the tooth whitening composition might occur during the operation which forms the slit 40, as discussed more fully hereafter. The ratio of the exposed surface area to volume of the thin layer 124 of the tooth whitening composition of the tooth whitening system 129 is relatively less than that of the thin layer 24 of the tooth whitening system 20 due to the relatively larger volume of the thin layer 124 of the tooth whitening composition from the addition of the second section 48 versus the relatively smaller increase in exposed surface area 50 from the addition of the second section 48 of the thin layer 124 of the tooth whitening composition.

Figure 7:
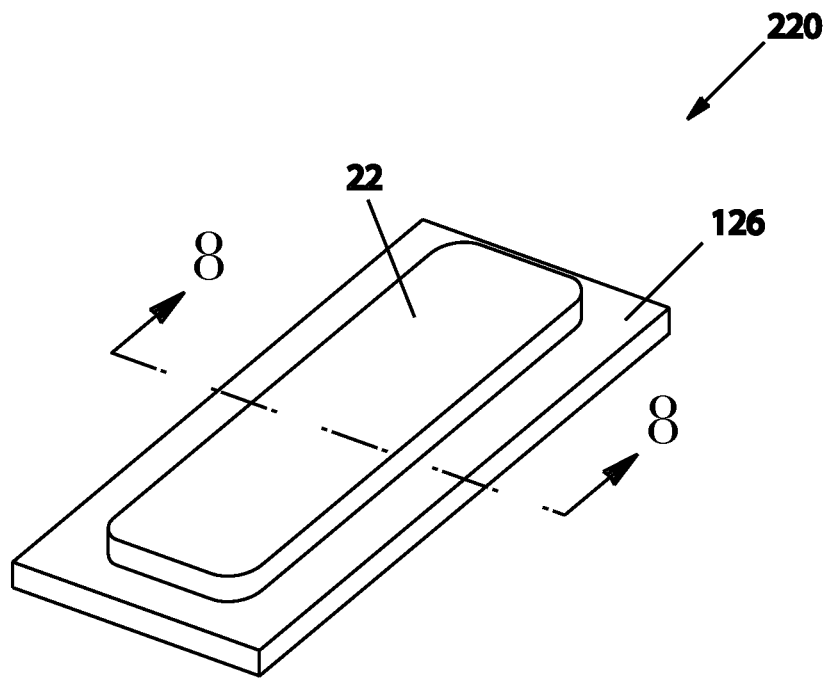
FIG. 7 is a perspective view of yet another preferred tooth whitening system made in accordance with the present invention.
Figure 8:
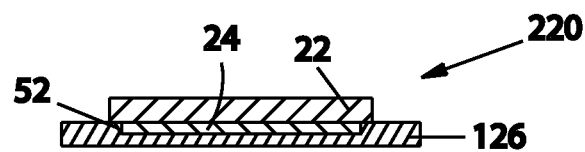
FIG. 8 is a cross-sectional side elevational view of the tooth whitening system of FIG. 7, taken along line 8-8 thereof.

Referring to FIGS. 7 and 8, another preferred embodiment of the present invention is illustrated in the form of a tooth whitening system 220. The tooth whitening system 220 comprises the substrate 22, the thin layer 24 of the tooth whitening composition, and a carrier 226 having a depression 52 therein. The thin layer 24 of tooth whitening composition is substantially encircled by the depression 52 and a portion of the substrate 22, thereby minimizing the ratio of the exposed surface area of the thin layer 24 to the volume of the thin layer 24. In a practical sense, the exposed surface area of the thin layer 24 is zero since is completely encircled by the depression 52 and the substrate 22 such that none of the tooth whitening composition would be exposed to the headspace of a package. The substrate 22 and carrier 126 are preferably directly adjacent each other outside of the depression 52, as best seen in FIG. 8, although it is contemplated that the substrate 22 might merely extend to the edge of the depression 52.

Figure 9:
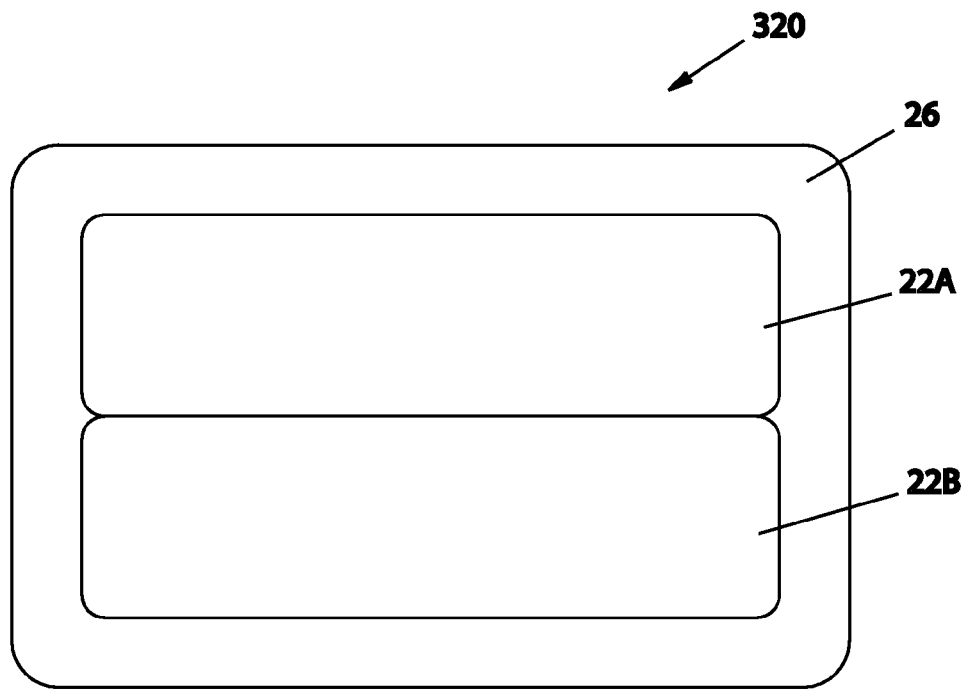
FIG. 9 is a top planar view of still yet another preferred tooth whitening system made in accordance with the present invention.
Figure 10:
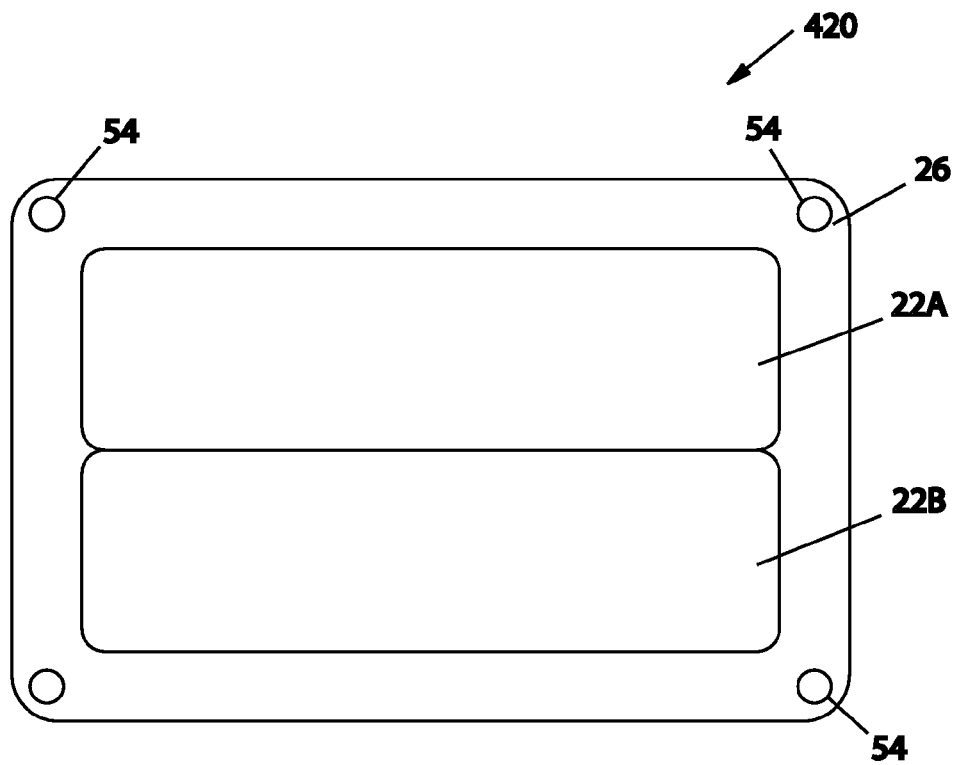
FIG. 10 is a top planar view of a further preferred tooth whitening system made in accordance with the present invention.

Referring to FIG. 9, yet another preferred embodiment of the present invention is illustrated. The tooth whitening system 320 comprises a carrier 26, two substrates 22A and 22B, and thin layers (not shown) of the tooth whitening composition. The substrates 22A and 22B preferably lie adjacent each other to minimize the size of the package storing the tooth whitening system 320. The size and shape of the substrates 22A and 22B are selected to provide the previously described values for the ratio of the exposed surface area to volume of the tooth whitening composition. Depending upon the shape and size of the substrates, the substrates 22A and 22B can be separated by a gap. Likewise, the thin layers and can be integrally formed or separated by a gap. The substrates 22A and 22B can be provided with similar or dissimilar shapes, as previously described with respect to the tooth whitening system 20. Where more than one substrate is provided in a single package 34, the exposed surface area and the volume of the tooth whitening composition of the tooth whitening system is the sum of the contributions from the thin layers 24A and 24B associated with each substrate within the package.

Figure 11:
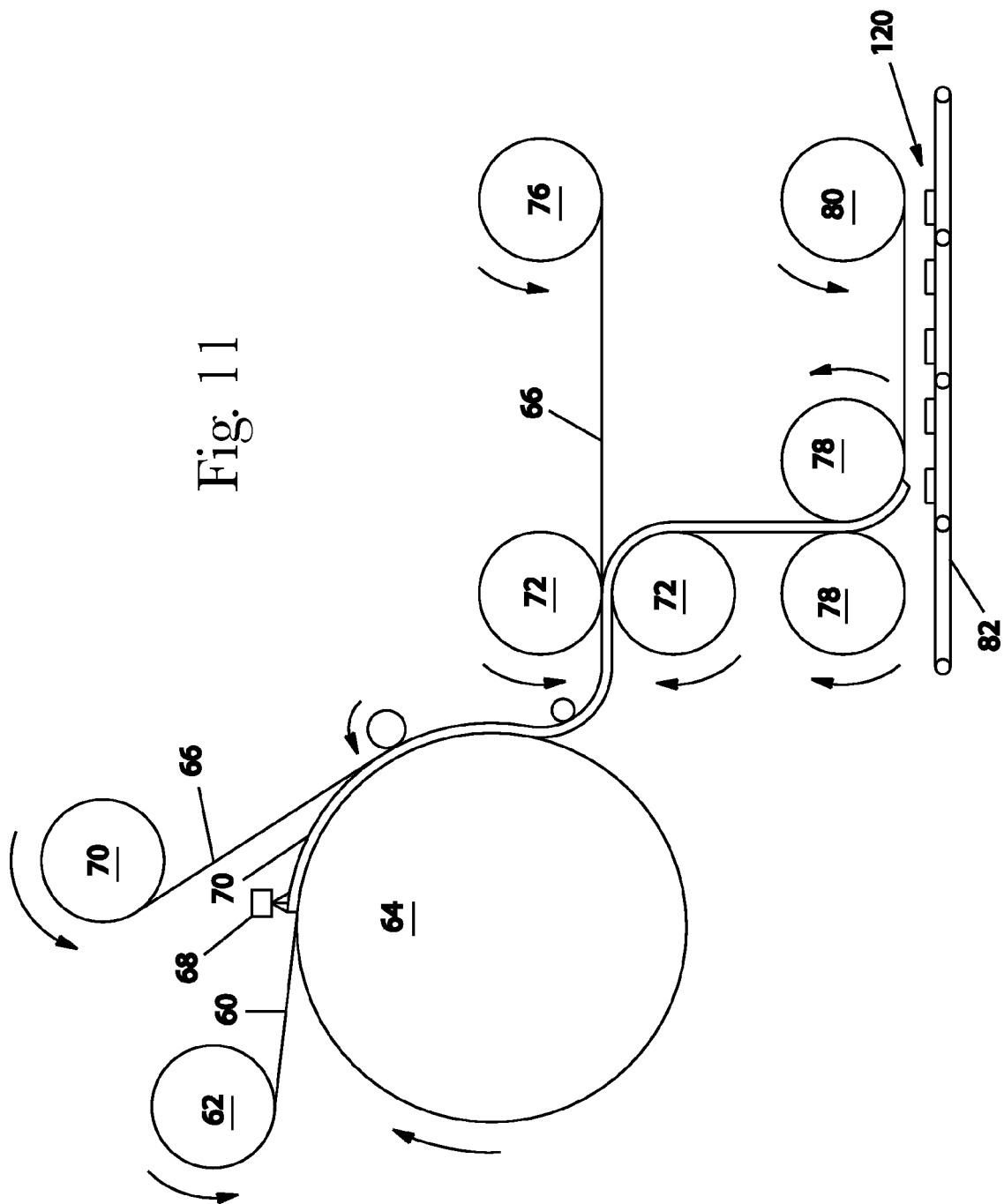
FIG. 11 is a schematic illustration of a method for manufacturing the tooth whitening system of FIG. 1.

In addition to the foregoing embodiments, the it is contemplated that the stability of the peroxide active of the thin layer 24 of the tooth whitening composition can be improved by the addition of another composition containing a peroxide active to the head space of a package, thereby increasing the exposed surface area of the tooth whitening system. Referring to FIG. 11 by way of example, the tooth whitening system 420 could comprise one or more groups 54 of a peroxide containing composition having a surface exposed to the head space of a package. The groups 54 can be provided as films, hemispherically-shaped groups, polyhedral shaped groups, or any other shape and size. While the groups 54 are illustrated as disposed on the carrier 26, it is contemplated that one or more groups might be disposed on an interior wall 56 (see, e.g., FIG. 3) of a package, or one or more groups might be disposed on a sheet or another carrier within the headspace 32 of a package 34.

Figure 2:
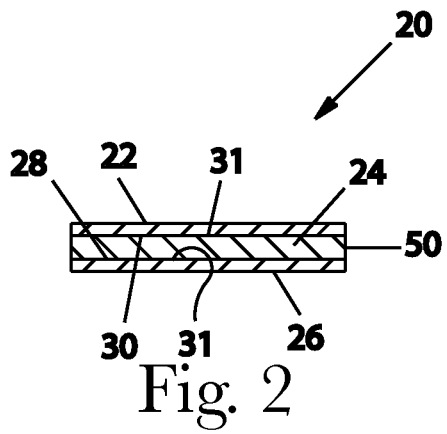
FIG. 2 is a cross-sectional side elevational view of the tooth whitening system of FIG. 1, taken along line 2-2 thereof.

In accordance with a still further aspect of the present invention, it has been found that the stability of the peroxide active can be improved by appropriate selection of the unexposed surface areas of the thin layer 24 and volume of the thin layer 24. As used herein, the term "unexposed surface area" is intended to refer to the surface areas which are not directly exposed to the headspace of a package, such as the surface areas 31 (FIG. 2) which are disposed adjacent the substrate 22 and the carrier 26. The ratio of the unexposed surface area of the thin layer 24 to the volume of the thin layer 24 is less than about 105 cm$^{-1}$ and, more preferably, is between about 40 cm$^{-1}$ and about 100 cm$^{-1}$. Most preferably, the ratio of the unexposed surface are of the thin layer 24 to the volume of the thin layer 24 is between about 60 cm$^{-1}$ and about 85 cm$^{-1}$.

In general, a tooth whitening system having one of a polyol concentration of less than about 40%, a ratio of the exposed surface area of the thin layer 24 to the volume of the thin layer of less than about 0.15 mm$^{-1}$, a ratio of the unexposed surface area of the thin layer to the volume of the thin layer of less than about 105 cm$^{-1}$, or the material forming the surfaces of the substrate 22 and the carrier 26 which is in contact with the tooth whitening composition are polyolefins can have between about 45% and about 70% of the original concentration of the peroxide active present at twelve months after manufacture. Optionally, such a tooth whitening system would have between about 50% and about 60% of the original concentration of the peroxide active present at twelve months after manufacture.

It has been found that the largest increases in stability of the peroxide active are from decreasing the concentration of the polyol or decreasing the value of the ratio of the exposed surface area of the thin layer 24 to the volume of the thin layer. Lesser increases in the stability of the peroxide active are achieved by the carrier and substrate material and decreasing the value of the ratio of the unexposed surface area of the thin layer to the volume of the thin layer 24.

A tooth whitening system having one or more of a polyol concentration of less than about 40%, a ratio of the exposed surface area of the thin layer 24 to the volume of the thin layer of less than about 0.15 mm$^{-1}$, a ratio of the unexposed surface area of the thin layer to the volume of the thin layer of less than about 105 cm$^{-1}$, and the material forming the surfaces of the substrate 22 and the carrier 26 which is in contact with the tooth whitening composition are polyolefins has between about 45% and about 100% of the original concentration of the peroxide active present at twelve months after manufacture. Optionally, such a tooth whitening system has between about 45% and about 85% of the original concentration of the peroxide active present at twelve months after manufacture. Other embodiments of such a tooth whitening system may have between about 50% and about 75% of the original concentration of the peroxide active present at twelve months after manufacture or between about 50% and about 70% of the original concentration of the peroxide active present at twelve months after manufacture.

Referring to FIG. 11, a preferred method for forming the tooth whitening system 120 will now be described. As will be appreciated, this method can also be adapted to manufacture the other preferred tooth whitening systems described herein. A sheet 60 of the carrier 26 is unrolled from the roller 62 and is fed over drum 64. The sheet 60 of the carrier 26 may be formed by several of the film making processes known in the art. The sheet 60 of the carrier 26 (as well as sheet 66 of the substrate 22) may be formed by several of the film making processes known in the art. The sheets 60 and 66 can be made by a blown process or a cast process. Processes, such as extrusion and other processes that do not affect the flexural rigidity of the substrate might also be used. A nozzle 68 sprays a thin layer 70 of the tooth whitening composition onto the sheet 60 of the carrier 26. The sheet 66 of the substrate 22 is unrolled from the roller 70 and lightly pressed onto the thin layer 70 of the tooth whitening composition, thereby forming a three layer laminate. The laminate is fed to the rollers 72 which create the slit 40 as well as cut through the sheet 66 of the substrate 22 and the thin layer 70 of the tooth whitening substance 22 to define the outer edges 74 (FIG. 5) of the second sections 38 and 48 thereof. After the cutting and slitting operation at rollers 72, the excess sheet 66 of the substrate 22 is taken up by the roller 76, thereby leaving the first and second sections of the substrate 22 and the tooth whitening composition on the sheet 60 of the carrier 26. The rollers 78 cut the carrier 26 to form individual tooth whitening systems 120. The excess carrier 26 is taken up by the roller 80 while the tooth whitening systems 120 are collected by the conveyor 82, after which the tooth whitening systems can be inserted into a package 34 to form a packaged peroxide product. As will be appreciated, these steps can be rearranged, deleted, and other steps added as is known in the art.

In general, after manufacture, the tooth whitening system 20 is stored in the package 34 (and/or in a secondary package or packages) at least about twelve months between about 20° C. and about 45° C. and substantially in the absence of light, although it is contemplated that at least a portion of this storage time (typically two to four months) can occur under refrigeration. More preferably, the tooth whitening system is stored at about room temperature (e.g., about 25° C.) in the absence of light. After storage, the package 34 can be opened by a user and the tooth whitening system is removed from the package 34. Following storage and after application of the tooth whitening composition to the teeth using the substrate 22, at least a portion of a tooth (and more desirably an entire tooth) will be whitened. As used in this patent, the term "whitening" is intended to refer to the delta or change in tooth color using the CIE LAB measurement methodology described in this patent.

After storage, the tooth whitening composition is applied to the teeth for between about 5 minutes and 120 minutes a day, preferably from about 30 minutes to about 60 minutes. Generally, this is done at least once a day for between about 7 days and about 28 days and more preferably twice a day between about 7 and about 14 days. The amount of time and the number of days within this regimen are dependent upon several factors, including the amount of whitening or bleaching desired, the wearer's teeth, and if initial or maintenance whitening or bleaching is desired. Thus, the total number of applications is between about 1 and about 42 and, more preferably, between about 5 and about 28. After storage for twelve months and application of the above-described regimen, a tooth whitening system provides a delta b* value less than or equal to: about −1, about −1.25, about −1.5, or about −2, wherein the minus sign signifies a direction along the b* axis in the negative direction (i.e., less yellow in the CIE LAB color space). More preferably, the delta b* is between about −1.25 and about −5 and most preferably the delta b* value is between about −2 and about −5. The delta L value is less than or equal to: about −1, about −1.25, about −1.5, or about −2, wherein the minus sign signifies a direction along the L axis in the negative direction (i.e., increasing brightness in the CIE LAB color space). More preferably, the delta L value is between about −1.25 and about −5 and most preferably the delta L value is between about −2 and about −5. The delta a* value is between about −3 and about +3, wherein the plus sign and minus sign signify directions along the a* axis in the positive and negative directions, respectively. Because the color of teeth can vary according to geography for dietary reasons, the delta a* value may correspondingly increase or decrease depending upon geography. The delta e value (which is defined in the art as the square root of the sum of the squared delta L, delta a*, and delta b* values) is between about 1 and about 7.7.

EXAMPLES

Examples of preferred tooth whitening compositions made in accordance with the present invention are described in the tables below. All ingredients in the tooth whitening compositions below should be mixed until homogeneous.

|  | 1 | 2 | 3 | 4 | 5 | 6 |
|---|---|---|---|---|---|---|
| Glycerin | 10.000% | 10.000% | 20.000% | 10.000% | — | — |
| Water | 67.776% | 64.348% | 54.348% | 64.248% | 74.148% | 67.776% |
| Hydrogen Peroxide (35% Solution) | 15.143% | 18.571% | 18.571% | 18.571% | 18.571% | 15.143% |
| Carboxypolymethylene | 4.500% | 4.500% | 4.500% | 4.500% | 4.500% | 4.500% |
| Sodium Hydroxide (50% Solution) | 2.000% | 2.000% | 2.000% | 2.000% | 2.000% | 2.000% |
| Sodium Saccharin | — | — | — | 0.100% | 0.200% | — |
| Sodium Stannate | 0.200% | 0.200% | 0.200% | 0.200% | 0.200% | 0.200% |
| Sodium Pyrophosphate | 0.381% | 0.381% | 0.381% | 0.381% | 0.381% | 0.381% |
| Propylene Glycol | — | — | — | — | — | 10.000% |
| Pluronic 407 | — | — | — | — | — | — |

|  | 7 | 8 | 9 | 10 | 11 | 12 |
|---|---|---|---|---|---|---|
| Glycerin | 10.000% | — | 3.000% | 15.000% | 10.000% | 10.000% |
| Water | 68.157% | 57.276% | 72.576% | 63.076% | 72.919% | 66.955% |
| Hydrogen Peroxide (35% Solution) | 15.143% | 15.143% | 17.143% | 15.143% | — | 17.143% |
| Carboxypolymethylene | 4.500% | — | 4.500% | 4.500% | 4.500% | 4.500% |
| Sodium Hydroxide (50% Solution) | 2.000% | 2.000% | 2.200% | 1.700% | 2.000% | — |
| Sodium Saccharin | — | — | — | — | — | — |
| Sodium Stannate | 0.200% | 0.200% | 0.200% | 0.200% | 0.200% | — |
| Sodium Pyrophosphate | — | 0.381% | 0.381% | 0.381% | 0.381% | — |
| Propylene Glycol | — | — | — | — | — | — |
| Pluronic 407 | — | 25.000% | — | — | — | — |
| Potassium Hydroxide | — | — | — | — | — | 1.403% |
| Carbamide Peroxide | — | — | — | — | 10.000% | — |

Method for Determining Percentages and Concentrations of Peroxide Actives

Values of peroxide active percentages and concentrations disclosed herein are measured using the following method. The package containing the peroxide system is stored for the stated period of time (e.g., 12 months) and conditions. After the stated storage time period, the peroxide concentration is measured using the Iodometric titration method. The Iodometric titration method is a standard method known in the art for measuring peroxide concentration. In general, the method is performed by weighing the substrate and composition containing the peroxide active, dissolving the composition in 1M sulfuric acid, and reacting the peroxide with an excess of potassium iodide in the presence of ammonium molybdate. This is then titrated with a known concentration of sodium thiosulfate to a clear endpoint using a starch indicator. The substrate is weighed upon completion of the titration and the composition weight is determined by difference. The peroxide concentration in the composition is then calculated. When the storage period is long, the concentration of the peroxide active can alternatively be determined by measuring the concentration as described above after at least one hundred and twenty days and then extrapolating for the remainder of the period using first order kinetics, as is known in the art. The above-described method is performed just after manufacture of a peroxide product and at the end of the specified storage period in order to determine the absolute peroxide concentrations as well as the percentage of the original concentration remaining, as is known in the art.

Method for Determining Whitening

Whitening herein can be measured according to the 1976 CIE LAB color space, wherein the L value measures brightness and varies from a value of one hundred for perfect white to zero for black. The a* value measures redness when positive, gray when zero and greenness when negative. The b* value measures yellowness when positive, gray when zero and blueness when negative. The L a* b* values herein can be measured using a spectrophotometer as known in the art, wherein the same lighting conditions are used for the first measurement prior to whitening and the second measurement after whitening. A spectrophotometer suitable use is the Photo Research Spectrascan PR650 manufactured by Photo Research, Inc. of Chatsworth, Calif. The lighting is provided by white light sources. The light sources should provide vertically polarized light, such as by use of polarizing filters. Filters suitable for use are HN 38 polarizing filters manufactured by 3M Corporation of Minneapolis, Minn. Other filters, such as an infrared reflecting filter of a filter to increase the color temperature of the light source, can be used. Suitable light sources are manufactured by Dedo Electric of Crystal Falls, Mich. and which are each fitted with a 150 watt, 24 volt Xenophot HLX bulb manufactured by Osram of Germany. Other polarized white light sources can be used as is known in the art. The light sources are placed 14 inches apart with the spectrophotometer disposed in between the light sources. The light sources are focused on a chin rest which is 12 inches from the lens of the spectrophotometer. The dimensional arrangement of the light sources, spectrophotometer, and the chin rest can be varied to accommodate the focal characteristics of various spectrophotometers. The lights are angled at approximately 45 degrees to focus on the chin rest. The spectrophotometer is set to L*, a* b* mode and calibrated against a white standard, as is known in the art. To measure tooth color, the subject positions his chin on the chin rest and lip retractors are used to pull the cheeks back and allow the light sources to illuminate the teeth.

Two whitening measurements are taken, wherein each whitening measurement measures the color characteristics of the subject tooth by focusing the spectrophotometer on the center of the tooth. For most tooth whitening systems, the central maxillary incisors are the teeth which are whitened. If the tooth whitening system is used to whiten more than one central maxillary incisor, then each measurement involves measuring the L a* b* values for not more than four of the central maxillary incisors to which the tooth whitening system is applied. The L a* b* values for these central four maxillary incisors are averaged to arrive at a single set of values for L a* b*. The first measurement is taken prior to application of the tooth whitening system and the second measurement is taken after application and removal of the tooth whitening system (i.e., after the whitening has occurred). Delta L a* b* values are the differences between the first and second measurements.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A tooth whitening system comprising:
 (a) a carrier;
 (b) a first discrete substrate and a first tooth whitening composition;
 (c) a second discrete substrate and a second tooth whitening composition; and
 (d) a package;
 wherein the first and second tooth whitening compositions are disposed on the carrier.

2. The tooth whitening system of claim 1, wherein said substrates are separated by a gap on said carrier.

3. The tooth whitening system of claim 1, wherein said substrates lie adjacent to each other on said carrier.

4. The tooth whitening system of claim 1, wherein one of said substrates is sized to fit at least a portion of an upper row of teeth, and one of said substrates is sized to fit at least a portion of a lower row of teeth.

5. The tooth whitening system of claim 4, wherein one of said substrates is sized to fit an upper front row of from about six to about eight teeth, and one of said substrates is sized to fit a lower front row of from about six to about eight teeth.

6. The tooth whitening system of claim 1, wherein said first and second tooth whitening compositions comprise a peroxide active.

7. The tooth whitening system of claim 1, wherein said first substrate and said first tooth whitening substance have an overall thickness of less than 1 mm.

8. The tooth whitening system of claim 1, wherein the first and second substrates comprise a barrier.

9. The tooth whitening system of claim 1, wherein the first and second substrates have different shapes.

10. The tooth whitening system of claim 1, wherein the substrates are in the form of a strip, tray, or combination thereof.

11. The tooth whitening system of claim 10, wherein the substrates are in the form of a strip.

12. A tooth whitening system comprising:
 (a) a carrier;
 (b) a first discrete substrate and a first tooth whitening composition; and
 (c) a second discrete substrate and a second tooth whitening composition
 wherein the tooth whitening compositions are disposed on the carrier.

13. The tooth whitening system of claim 12, wherein one of said substrates is sized to fit at least a portion of an upper row of teeth, and one of said substrates is sized to fit at least a portion of a lower row of teeth.

14. The tooth whitening system of claim 13, wherein one of said substrates is sized to fit an upper front row of from about six to about eight teeth, and one of said substrates is sized to fit a lower front row of from about six to about eight teeth.

15. The tooth whitening system of claim 12, wherein the first and second substrates have different shapes.

16. The tooth whitening system of claim 12, wherein the substrates are in the form of a strip, tray, or combination thereof.

17. The tooth whitening system of claim 16, wherein the substrates are in the form of a strip.

18. A tooth whitening system comprising:
 (a) a carrier;
 (b) a first discrete substrate in the form of a strip and a first tooth whitening composition; and
 (c) a second discrete substrate in the form of a strip and a second tooth whitening composition;

wherein the first and second tooth whitening compositions are disposed on the carrier and the carrier is capable of being separated from the tooth whitening compositions prior to application.

19. The tooth whitening system of claim 18, wherein the tooth whitening compositions lie adjacent to each other on the carrier.

20. The tooth whitening system of claim 18, wherein the first and second substrates have different shapes.

* * * * *